United States Patent

Kahng et al.

[11] Patent Number: 5,817,954
[45] Date of Patent: Oct. 6, 1998

[54] AUTOMATED ANALYZING APPARATUS FOR MEASURING WATER QUALITY WITH A CYLINDER-SHAPED SYRINGE UNIT

[75] Inventors: Sung Hyun Kahng; Sung Rok Cho; Soo Hyung Lee; Eun Soo Kim; Kun Young Lee, all of Kyonggi-do; Jae Ryoung Oh, Seoul, all of Rep. of Korea

[73] Assignee: Korea Ocean Research & Development Institute, Rep. of Korea

[21] Appl. No.: 750,701

[22] PCT Filed: Oct. 8, 1996

[86] PCT No.: PCT/KR96/00172

§ 371 Date: Dec. 16, 1996

§ 102(e) Date: Dec. 16, 1996

[87] PCT Pub. No.: WO97/14039

PCT Pub. Date: Apr. 17, 1997

[30] Foreign Application Priority Data

Oct. 9, 1995 [KR] Rep. of Korea .................. 1995-34589
Oct. 2, 1996 [KR] Rep. of Korea .................. 1996-43677

[51] Int. Cl.⁶ .................................................. G01N 1/00
[52] U.S. Cl. .......................................... 73/863.84; 422/75
[58] Field of Search ........................... 73/864.81, 864.35, 73/863.84, 864.56; 422/75–77, 62, 63

[56] References Cited

U.S. PATENT DOCUMENTS 3,160,477 12/1964 Wasilewski ............................... 422/75
4,165,218 8/1979 Vanhumbeeck et al. ................. 422/75
4,459,865 7/1984 Welker .................................. 73/864.62
4,476,095 10/1984 Scott et al. ................................ 422/75

FOREIGN PATENT DOCUMENTS 0 185 334 A2 6/1986 European Pat. Off. .
39 34 024 A1 4/1991 Germany .

*Primary Examiner*—Robert Raevis
*Attorney, Agent, or Firm*—Beveridge, DeGrandi, Weilacher & Young, LLP

[57] ABSTRACT

The present invention provides an automated analyzing apparatus which comprises: a syringe unit for inhaling or transfering liquid such as sample, reagents and washing solution by moving the piston (12) by a certain distance; a built-in stirring bar (31) located within the syringe barrel (11); a driving unit for rotating the stirring bar (31); a driving means (13) for moving the piston (12) up and down; several connection paths (15a–15f) located in the lower part of the syringe barrel (11) or in the piston (12) where the sample, the reagents, the washing solution, and air can be provided or discharged; 2-way on/off valves (16a–16f) connected to each connection path (15a–15f); detecting means (3) positioned in the outer wall of the syringe barrel (11) perpendicular to the piston shaft (14); additional heating and cooling unit (4) for temperature control or sample digestion; control unit (6) for controlling the driving means (13), the detector (2) and valves (16a–16f) described above.

11 Claims, 2 Drawing Sheets

AUTOMATED ANALYZING APPARATUS FOR MEASURING WATER QUALITY WITH A CYLINDER-SHAPED SYRINGE UNIT

TECHNICAL FIELD

The present invention relates to an automated analyzing apparatus for measuring chemical constituents or contaminants contained in liquid samples. More particularly, this invention relates to a simple and versatile analyzer suitable for real-time water quality monitoring.

BACKGROUND ART

In the area of water and wastewater analysis, measurements of dissolved oxygen, inorganic nutrients, chemical oxygen demand (COD), total phosphorus, total nitrogen, major cations and anions, toxic organics, and trace metals are frequently used.

Conventionally, since the water quality measurements noted above are conducted in the laboratory after a sample was taken and transferred except certain constituents and physical parameters, immediate analysis in the field is required. The introduction of unmanned automatic analyzers, however, has made it practical to get continuous or semi-continuous data directly from the field. Water quality monitoring on a real-time basis has been realized by employing a wired or a wireless telemetry data aquisition system. A fully automated analyzing system installed in the field can reduce manpower, time, cost, etc., as well as provide a huge amount of water quality data that helps to monitor a water's current status and long-term trends. Many applications of automatic water quality monitoring have been made, such as: monitoring of effluent discharged from point sources; oceanographic survey covering large geographic area using the ship-of-opportunity; water quality monitoring buoy moored at a fixed location; concurrent water quality measurement at multiple places. Unmanned water quality measuring apparatuses currently being used carry out the experimental procedures that simulate human operation. They generally consist of a sampling unit, a mixing chamber, a reaction vessel, a liquid delivering means, reservoirs for sample and reagents, detectors, power supplies, and control units.

The conventional automatic analyzing apparatus is arranged so as to collect a sample from the sources, mix the sample with some reagents supplied from reservoirs by liquid delivering pumps, make the sample and reagents react in a reaction vessel under a specific condition, measure the concentration by a detector, and then discharge the reactants with the aid of pump. A heating and a cooling chambers, if necessary, can be installed to digest the sample or to speed up the reaction. The conventional automatic analyzing apparatus also can be designed so that a series of experimental procedures and conditions are preset and controlled by microprocessors or computers.

Automatic and quantitative delivery of liquids in the predescribed apparatus has been convenienced by employing peristaltic pumps, known device for providing pockets of fluid. The peristaltic pump, for example, may have the construction shown in U.S. Pat. Nos. 3,358,609 and 4,233,001. In general, an automatic analyzing apparatus requires several peristaltic pumps at each fluid path, which results in a high production cost of instrument as well as an oversized volume and weight. Due to its large size and large electric power requirement, a field station or a specially designed vessel or buoy having a large enough space and power supply must be constructed in order to install several automatic analyzers in the field. In some autoanalyzers, an inert gas source and fast-acting solenoid valves are used to transfer liquid from the pressurized reservoirs to the reaction chambers (for example, disclosed in U.S. Pat. No. 4,920,056). One or more automatically actuated solenoid valves are used to introduce respective pressurized reagents into the reaction chamber to process the sample. The volume of the reagents introduced into the reaction chamber is controlled by a valve opening time of the respective reagent valve. Since flow rate and volume of the reagent wholly depend on pressure of reservoirs and valve opening time, it is very difficult to accurately dispense liquids whose viscosity changes as temperature varies.

In order to improve the drawbacks of conventional automated water quality analyzers, a syringe photometer was disclosed in EP 0185334 A2. This photometer comprises: a syringe pump with a cylinder head and a piston; a motor for moving the piston back and forth; a separate unit for mixing a sample and reagents adequately; and a light source and a photodetector that are parallel with a piston shaft and located at the cylinder head and the piston respectively. This syringe photometer is compositionally simpler than a conventional automatic analyzer having peristaltic pumps, while its applications are limited in colorimetric determination.

The syringe photometer, however, has significant problems in application as a versatile automated water quality analyzer. The syringe photometer does not have a stirring function in itself, so either a subsidiary mixing pump, a mixing chamber, or an additional syringe pump must be added to mix the sample with the reagents adequetely. Futhermore, a repeated give-and-take between the syringe photometer and the subsidiary mixing unit through the connection tube may be required in order to mingle the mixtures sufficiently.

Lack of a stirrer in itself makes it impossible to carry out volumetric analysis which depends on the measurement of liquid reagent volumes of standard solutions needed to complete particular reactions in samples submitted for testing. In order to titrate the sample with a standard solution, a small amount of reagent must be added and mixed repeatedly until the stoichiometric end point has been reached. But the subsidiary mixing unit described above limits the applicability of the syringe pump to this kind of analysis.

Another fundamental defect found in the syringe photometer is that both the light source and the photo-detector directly make contact with a liquid, so they are likely to be contaminated because sample, reagents and its colored complex are inflowed into the inside of piston pump. In many cases, colored compounds or complexes prepared for photometric determination are likely to adhere to the solid surface, and such fouling of the detector and the light source may cause a baseline drift and a sensitivity decrease in the analyser. Thus, frequent manual washing of the piston pump is necessary, which makes it hard to maintain the automated machine in the field.

DISCLOSURE OF INVENTION

In contrast to the automatic water quality analyser noted above, the present invention intends to offer a new system or apparatus which features simplicity in configuration and integrated functions of fluid handling, mixing and detection.

To achieve the above intention, the present invention provides an automated analyzing apparatus which includes a simple cylinder-shaped syringe unit equipped with a stirrer and detectors. Particularly, this syringe performs the multifunctions of a pump, a mixing chamber, a reaction vessel, a measuring device, a titrator, a diluter and a detector.

An embodiment of the present invention comprises:

a syringe unit having a syringe barrel in which a sample, reagents, a washing solution and air are provided or discharged and a piston which is inserted inside the syringe barrel to form varible sealed space;

a stirring means located within the syringe barrel for mixing solution;

a driving means for moving the piston up and down, connection paths through which the sample, reagents, a washing solution, and air can be provided to or discharged from the syringe barrel;

2-way on/off valves connected to each connection path;

a detecting means positioned perpendicular to a shaft of the piston on the outer wall of the syringe barrel;

and a control unit for controlling the stirring means, the driving means, the detecting means and the valves described above.

In accordance with this invention, the syringe unit can inhale or discharge accurate amounts of a selected liquid by moving the piston up and down, when 2-way on/off valves equipped in the connection paths are selectively opened or closed. The stirring means disposed in the lower part of the syringe barrel enables a stirring bar within the syringe barrel to mix the sample with reagents thoroughly and quickly. Separated reagent intakes furnished with 2-way on/off valves are disposed to the piston itself or to the lower part of syringe barrel, which prevents contamination by reagents.

In accordance with this invention, the syringe unit integrated with the stirring means can be used as a titrator, which makes it possible to carry out not only calorimetric detection, but also diverse volumetric analyses such as potentiometric analysis, coulometric analysis, and photometric titration analysis, etc. In addition, the arrangement of a photometric or fluorometric light source and a detector perpendicular to a shaft of the piston on the outer wall of the syringe barrel has the advantage of preventing possible fouling of the light path because repeated strokes of syringe barrel always cleanse the inner wall of the syringe barrel. This feature guarantees a long-term operation without manually cleaning the syringe barrel.

Other aspects and various advantages of the present invention will become apparent through the following description of embodiments thereof with reference to the drawings.

BRIEF DESCRIPTION OF DRAWINGS

The accompanying drawings, which are incorporated in and constitute a part of the specification, illustrate an embodiment of the invention, and together with the description, serve to explain the principles of the invention.

BEST MODE FOR CARRYING OUT THE INVENTION

Embodiment 1

Figure 1:
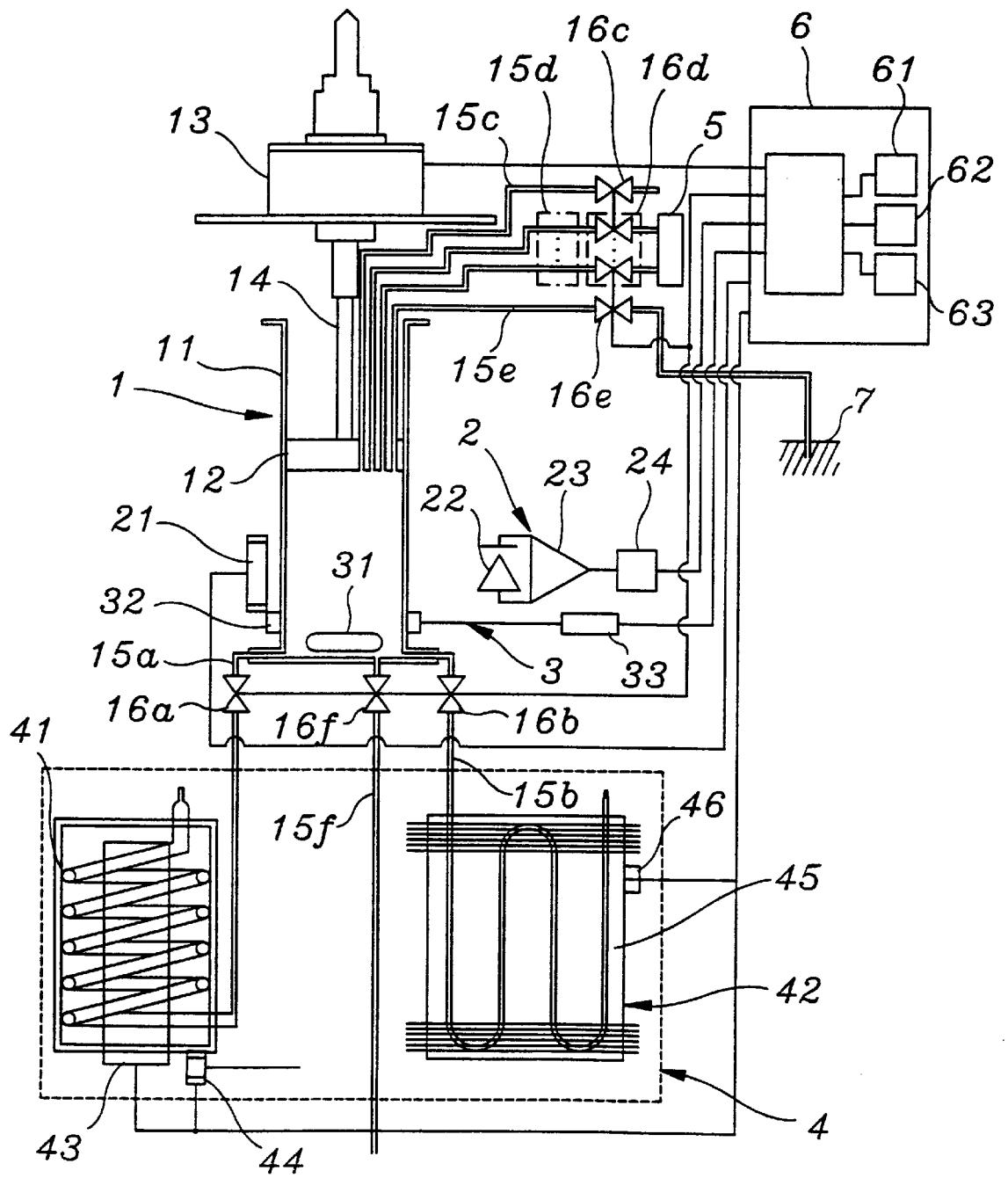
FIG. 1 shows a schematic diagram of an automated analyzing apparatus according to the present invention.

With reference to FIG. 1, automated analyzing apparatus according to the present invention comprises; a cylinder-shaped syringe unit 1 as both a reaction chamber and a liquid handling means for inhaling or transfering the sample, the reagents and the washing solution; a detector 2 for measuring intended analytical reactions conducted in the cylinder-shaped syringe unit 1; a stirrer 3 for mixing the reacting solution inside the cylinder-shaped syringe unit 1; a heating/cooling unit 4; a reservoir 5 for storing reagents and the washing solution; and main controller 6.

The heart of this invention is said cylinder-shaped syringe unit 1, which is arranged so that a piston 12 is inserted to form variable sealed space inside a syringe barrel 11. This piston 12 is moved up and down by a driving means 13 connected with a piston shaft 14. The sample, reagents, the washing solution, and air are provided or discharged through connection paths 15a–15f by the piston 12 strokes while solenoid valves 16a–16f are selectively opened or closed. Solenoid valves 16a–16f furnished to all connection paths 15a–15f are independently opened and closed by a microprocessor. The connection paths 15a–15f are disposed in the lower part of the syringe barrel 11 as well as through the piston 12 itself.

In the preferred embodiment, the syringe barrel 11 is made of transparent glass or quartz in order to avoid corrosion of its inner wall and adsorption of contaminants, where photometric detection is carried out. The piston 12 is also made of known material, for example PTFE, which guarantees corrosion resistance, watertightness and airtightness.

The driving means 13 moves the piston 12 up and down by a certain distances. While stepping motor or servo motor, etc. is available for driving means 13, the construction of the cylinder-shaped syringe unit 1 was simplified by using the linear actuator stepping motor, which rectilinearly moves motor shaft.

In order to prevent mixing or contamination among reagents, separated reagent intakes of connection paths 15a–15f are respectively furnished with solenoid valves 16a–16f and are positioned to the piston 12 itself or to the lower part of the syringe barrel 11. It is especially desirable to dispose connection paths 15a,15b to the lower part of the syringe barrel 11, because of fluid flow to the subsidiary heating and cooling chambers 41,42. The connention path for discharge outlet 15f is conveniently positioned at the bottom of the syringe barrel 11, while the connection path for air flow 15c is positioned at the piston 12.

Although the principal design of this invention is not restricted to any particular type of chemical analysis, the preferred embodiment described as part of an automated analyzing apparatus will be a device for photometric titration. The light source 21 and photodetector 22 may be of known devices for colorimetric determination, but they are arranged perpendicular to the piston shaft 14 and positioned face to face on the outside of the syringe barrel 11, which has the great advantage of preventing possible fouling of the light path because repeated strokes of the syringe barrel 11 always cleans the inner walls of the syringe barrel 11. This feature guarantees a long-term operation without manually cleaning the syringe barrel 11.

The stirrer 3 is also a known device for mixing the sample with the reagents. In the embodiment of the present invention, N/S conversion of a electomagnets 32 controlled by a stirrer controller 33 rotates a built-in stirring bar 31 within the syringe barrel 11 when as many electromagnets 32 as necessary are arranged around the syringe barrel 11. This built-in stirrer 31 enables the syringe barrel 11 to play the diverse roles of being a mixing chamber, a reaction vessel, a titrator and a detector.

All the reagents, the standard solution and the washing fluid are held in the containers in the reservoir 5, and their outlet from each container is connected to the syringe barrel 11 through connection path 15d equipped with solenoid valve 16d. Since the reagents and the washing solution will be delivered by the piston 12 movement, it is unnecessary to install peristaltic pumps, so the overall configuration is much simpler.

The purpose of said heating and cooling unit 4 is to control the reaction temperature or to digest the sample. They are also of a known construction which includes: a heating chamber 41 equipped with a heater 43 and a temperature sensor 44; and a cooling chamber 42 consisting of a cooling fan 45 and a temperature sensor 46. However, the invention's unique configuration, which allows the syringe barrel 11 to deliver a mixture to heating and cooling chamber 41,42 as well as to withdraw sample from the heating and cooling chamber 41,42, does not require additional peristaltic pumps to transfer liquids.

Due to the absence of peristaltic pumps, this system does not require much electric power, so solar cells and a condenser for a DC power supply may be used in the cases of geographically remote sites and of buoys floating on water.

The main controller 6 controls the individual units of the automatic analyzing appratus. A microprocessor has a series of commands programmed in advance and actuates the driving means 13, the solenoid valves 16a–16f, the detector 2, the stirrer 3, the heating/cooling unit 4, etc. The main controller 6 also comprises a data storage unit 61, a displaying unit 62, and a communication means 63, wherein measured data is stored, displayed and transmitted.

The basic operation of the automatic analyzing appratus using photometric titration according to the present invention is as follows. Firstly, the sample is sucked in by moving the piston 12 up the syringe barrel 11 when solenoid valve 16e is open. The sampling amount solely depends on the moving distance of the piston 12, which is proportional to the number of pulses sent to the stepping motor. The suction of other reagents and the washing solution from the reservoir 5 is also carried out in the same manner described above.

The stirrer controller 33 rotates the built-in stirring bar 31, and then the sample is mixed with reagents adequately. In order to digest the sample, the piston 12 is pushed down after opening a solenoid valve 16a, and then the mixed solution is transferred to the heating chamber 41. Delivery of the mixed solution is completed by a small stroke of the piston 12 to push air. The solenoid valve 16a is closed and the valve 16c is opened when the piston 12 is elevated. The solenoid valve 16a is opened and the valve 16c is closed when the piston 12 is pushed down. The digested sample in the heating chamber 41 is transferred into the cooling chamber 42 by actuating solenoid valves 16a, 16b, and 16c. When cooling is completed, then the digested solution is sucked again from the cooling chamber 42 and titrated by minutely elevating of the piston 12 and mixing of the reagent and the digested sample in series. During titration, the absorbance (transmittance) can be measured by passing light at a specific wavelength through the solution and detecting the amount of light passing through the sample. The stoichiometric end point can be found photometrically by adding a specific indicator or by measuring the amount of the colored compound directly proportional to the concentration of the substance of interest. After titration has finished, waste is discharged by moving down the piston 12.

Embodiment 2

Figure 2:
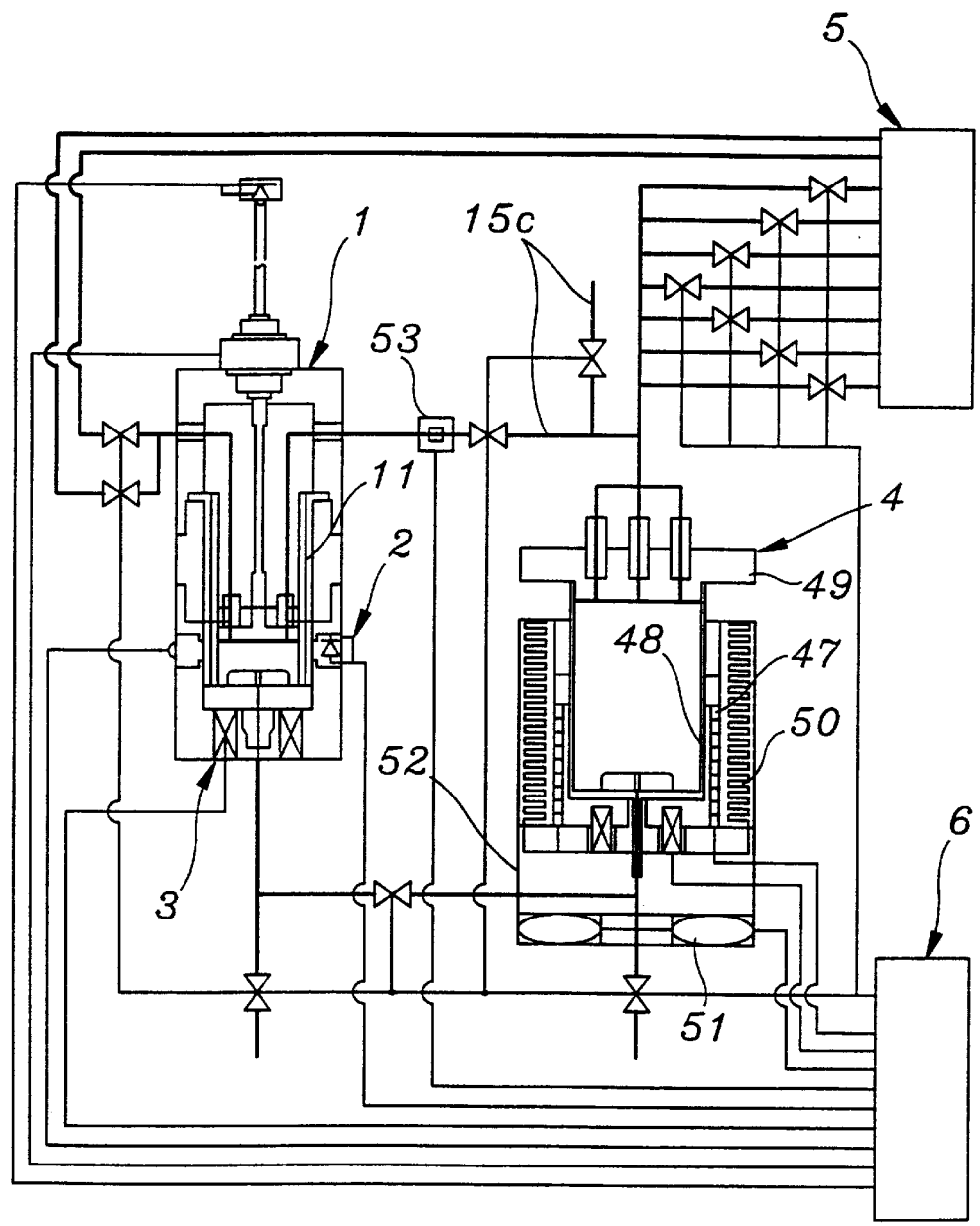
FIG. 2 shows another schematic drawing of an automated analyzing apparatus according to the present invention.

FIG. 2 shows the schematic configuration of an automatic analyzing apparatus according to the present invention equipped with a unified heating/cooling unit 4. The key to the design of the unit is the use of a Peltier effect thermomodule 47. The thermomodule 47 is a np-type semiconducter that has the ability to pump heat from one side to the other side when electricity is provided. The direction of heat pumping can be reversed according to the reversal of current direction.

The unified heating/cooling unit 4 is composed of:
a vessel 48 with a connention path on the bottom thereof; a cover 49 having several connection paths; a built-in stirring bar within the vessel 48; a driving unit for rotating the stirring bar; the thermomodule 47 surrounding the vessel 48; heat sinks 50 connected to the outer surface of the thermomodule 47; a fan 51 and a windbreak case 52 installed on the bottom of the heating/cooling unit 4; and a pressure sensor 53 installed in air connection path 15c.

The unified heating/cooling unit 4 has an advantage of heating and cooling in the same unit, and it also plays the role of a condenser because vapor condenses at and fall down from the upper part of the vessel 48. In the reverse mode, heat in the vessel 48 is pumped out to the heat sinks 50 and then excluded with the aid of the fan 51.

Compared to embodiment 1, the automatic analyzing appratus noted above has different configurations in that the drain of cylinder-shaped syringe unit 1 is connected to the drain of the unified heating/cooling unit 4. Embodiment 2 represents a differenct mode of operation, i.e., the sample, the reagents and the washing solution are directly introduced into the unified heating/cooling unit 4 through the connection paths of the cover 49, which makes the operation procedures simpler, and prevents the syringe barrel 11 from getting damaged by heat or corrosive chemicals.

However, in this case, the intake speed of liquid into unified heating/cooling unit 4 may be decreased.

To solve this problem, a method of pressurizing the reagents reservoir 5 can be used. Pressure sensor 53 is installed in the connention path and all the reagent containers of the reservoir 5 are pressurized by an inert gas or by a pump. First, the piston is elevated to a certain distance without opening the reagent inlet valve located in the heating/cooling unit 4. This operation induces a pressure decrease within the syringe barrel 11 and the heating/cooling unit 4. At this time reagent the inlet valve is opened, and a pressurized reagent is introduced into the heating/cooling unit 4. The inflow of the reagent will counterbalance the low pressure within the syringe barrel 11 and the heating/cooling unit 4. The inner pressure is continuously checked by a pressure sensor installed in the connention path, and the reagent inlet valve is closed when the inner pressure becomes identical with atmospheric pressure.

Therefore, this method allows the sample and the reagents to be taken into the syringe barrel 11 rapidly, and allows the connection paths not to be choked up.

A pressure device using this pressurizing method can be applied to all apparatuses of this invention. But, it is not necessary for all apparatuses to be installed with this apparatus. It is only necessary for this apparatus.

As an example of the construction noted above, an automatic analyzer for measuring chemical oxygen demand (COD) has been constructed. The COD is used to measure the oxygen equivalent of the organic matter contents of a sample that is susceptible to oxidation by a strong chemical oxidant. For a more complete description and discussion of COD measurement, see Standard Method of The Examination of Water and Wastewater, Clesceri, L. S. et al. (eds.), American Public Health Association, pps 5–10 et sec.

More specially, the present invention provides an preferred embodiments of COD autoanalyzer as follows.

Firstly, 5 ml of a water sample is introduced into the unified heating/cooling unit 4 by suction of the syringe barrel 11. 7 ml of sulfuric acid containing mecuric chloride and silver sulfate is added to the sample slowly and mixed by rotating the built-in stirring bar within the vessel 48. Electrical cooling is continued in the unified heating/cooling unit 4 during mixing in order to avoid possible loss of volatile materials. Then, 3 ml of potassium dichromate is added as a digestion solution. Temperature of the unified heating/cooling unit 4 is raised to 150° C. and refluxed for 2 hours. The digested sample is cooled to room temperature and transferred into the syringe barrel 11. 0.10 ml of a ferroin indicator solution is added and mixed. Excess potassium dichromate is titrated with a 0.10M standard ferrous ammonium sulfate (FAS) solution. While titrating with FAS, the digested sample is stirred rapidly by the built-in stirrer within the syringe barrel 11. Sharp color change at the end point from blue-green to reddish brown is detected by a photosensor. The amount of FAS used for the sample is recorded and the COD of the sample is calculated automatically. When all the analysis procedures are finished, waste is discharged through the drain by pushing down of the piston. The syringe barrel 11 and the heating/cooling unit 4 are cleaned up by sucking washing fluid for a next analysis.

INDUSTRIAL APPLICABILITY

This invention can be applied to new automated water quality analyzers. Since the cylinder-shaped syringe unit 1 results in functional integration of conventioanl components and in simplicity of configuration, it becomes possible to produce light-weight and inexpensive automated analyzers for real-time water quality monitoring. Advantages in size and price will accelerate the expansion of its use in related fields. The cylinder-shaped syringe unit 1 is highly versatile in application. It may also be feasible in the development of new instruments for analyzing diverse water quality parameters.

What is claimed is:

1. An automated analyzing apparatus for determining the amount of chemical constituents or contaminants contained in liquid samples comprising:

a syringe unit having a syringe barrel in which a sample, reagents, a washing solution and air are provided or discharged and a piston which is inserted inside the syringe barrel to form varible sealed space;

a stirring means located within the syringe barrel for mixing a solution;

a driving means for moving the piston up and down, connection paths through which the sample, the reagents, the washing solution, and air can be provided to or discharged from the syringe barrel;

2-way on/off valves connected to each connection path;

a detecting means positioned perpendicular to a shaft of the piston on the outer wall of the syringe barrel;

and a control unit for controlling the stirring means, the driving means, the detecting means and the valves described above.

2. The automated analyzing apparatus of claim 1, wherein said driving means is the linear actuator stepping motor that rectilinearly moves the motor shaft.

3. The automated analyzing apparatus of claim 1, wherein said stirring means is equipped with several electomagnets surrounding the syringe barrel for rotating a built-in stirring bar within the syringe barrel and is equipped with a control means for N/S conversion of the electromagnets.

4. The automated analyzing apparatus of claim 1, wherein said connection paths are located in the lower part of the syringe barrel or in the piston.

5. The automated analyzing apparatus of claim 1, wherein said detecting means is a light source and a photodetector which are arranged perpendicular to the piston shaft and positioned face to face on the outside of the syringe barrel.

6. The automated analyzing apparatus of claim 1, wherein inner space of the syringe unit is connected through connection paths to a subsidiary heating and cooling unit whose temperature is automatically controlled.

7. The automated analyzing apparatus of claim 6, wherein said heating and cooling unit is composed of:

a vessel for containing liquid;

thermomodules around the vessel for puming heat by the Peltier effect;

and a controller for switching the current direction of the thermomodule.

8. The automated analyzing apparatus of claim 7, wherein said heating and cooling unit is additionally equipped with a stirrer for mixing liquid.

9. The automated analyzing apparatus of claim 8, wherein said stirrer is equipped with several electomagnets around the vessel for rotating a built-in stirring bar within the vessel by N/S conversion of the electromagnets.

10. The automated analyzing apparatus of claim 7, wherein said heating and cooling unit is additionally connected to a reagents reservoir by connection paths.

11. The automated analyzing apparatus of claim 10, wherein said reagents reservoir is equipped with a pressure device which pressurizes the reservoir's inner space.

\* \* \* \* \*